United States Patent [19]

Walkup et al.

[11] Patent Number: 5,089,608
[45] Date of Patent: Feb. 18, 1992

[54] SELECTIVE 6-ACYLATION OF SUCROSE MEDIATED BY CYCLIC ADDUCTS OF DIALKYLTIN OXIDES AND DIOLS

[75] Inventors: Robert E. Walkup, Watkinsville; Nicholas M. Vernon; Robert E. Wingard, Jr., both of Athens, all of Ga.

[73] Assignee: McNeil-PPC, Inc., Milltown, N.J.

[21] Appl. No.: 499,731

[22] Filed: Mar. 23, 1990

[51] Int. Cl.$^5$ .................. C07H 1/00; C07H 13/02; G08B 37/00
[52] U.S. Cl. .................. 536/124; 536/121; 536/119; 536/115; 536/18.6; 536/17.1
[58] Field of Search ............... 536/119, 115, 121, 122, 536/124, 18.6, 4.1; 521/126; 548/403

[56] References Cited

U.S. PATENT DOCUMENTS

| | | | |
|---|---|---|---|
| 4,343,934 | 8/1982 | Jenner et al. | 536/122 |
| 4,360,670 | 11/1982 | Bechara et al. | 521/126 |
| 4,362,869 | 12/1982 | Jenner et al. | 536/122 |
| 4,380,476 | 4/1983 | Mufti et al. | 536/119 |
| 4,430,456 | 2/1984 | Bechara et al. | 521/128 |
| 4,464,490 | 8/1984 | Bechara et al. | 521/126 |
| 4,465,828 | 8/1984 | Rau et al. | 536/18.6 |
| 4,950,746 | 8/1990 | Navia | 536/119 |

OTHER PUBLICATIONS

Holzapfel et al., "Sucrose Derivatives and the Selective Benzoyolation of the Secondary Hydroxyl Groups of 6,1',6'-Tri-O-Tritylsucrose", S. Afr. Tydskr. Chem., 1984, 37(3), pp. 57-61.

David et al., Regioselective Manipulation of Hydroxyl Groups Via Organotin Derivatives, Tetrahedron, vol. 41, No. 4, pp. 643-663 (1985).

Primary Examiner—Johnnie R. Brown
Assistant Examiner—Everett White
Attorney, Agent, or Firm—Charles J. Metz

[57] ABSTRACT

There is disclosed a process which comprises the steps of:

(a) reacting a di(hydrocarbyl)tin oxide such as a dialkyltin oxide with a dihydric alcohol, alkanolamine, or an enolizable α-hydroxyketone in an inert organic reaction vehicle, with removal of water, at a temperature and for a period of time sufficient to produce a cyclic adduct of said dialkyltin oxide and said dihydric alcohol, alkanolamine, or enolizable α-hydroxyketone;

(b) reacting said cyclic adduct product of Step (a) with sucrose in an inert organic reaction vehicle such as a dipolar aprotic liquid, at a temperature and for a period of time sufficient to produce a 6-O-[dihydrocarbyl(hydroxy- or amino- or oxohydrocarbyl)stannoxyl]sucrose; and (c) reacting the product of Step (b) with an acylating agent to produce a sucrose-6-ester.

16 Claims, No Drawings

SELECTIVE 6-ACYLATION OF SUCROSE MEDIATED BY CYCLIC ADDUCTS OF DIALKYLTIN OXIDES AND DIOLS

The invention relates to a process for producing sucrose derivatives by a regioselective reaction, and can be used, for instance, to produce monosubstituted sucrose derivatives wherein the substituent is in the 6 position.

BACKGROUND OF THE INVENTION

The sucrose molecule contains three primary hydroxyl groups and five secondary hydroxyl groups. Therefore, when it is desired to prepare derivatives of sucrose involving reaction of the hydroxyl groups, it can be a major synthesis problem to direct the reaction only to the desired hydroxyl groups. For instance, the artificial sweetener 4,1',6'-trichloro-4,1',6'-trideoxyoalactosucrose ("sucralose") is derived from sucrose by replacing the hydroxyls in the 4, 1', and 6' positions with chlorine. (In the process of making the sweetener, the stereo configuration at the 4 position is reversed - hence the compound is a galactosucrose.) This compound and methods for synthesizing it are disclosed in U.S. Pat. Nos. 4,343,934, 4,362,869, 4,380,476, and 4,435,440. The direction of the chlorine atoms to only the desired positions is a major synthesis problem, especially since the hydroxyls that are replaced are of differing reactivity (two are primary and one is secondary; the synthesis is further complicated by the fact that the primary hydroxyl in the 6 position is unsubstituted in the final product). The preparation of this sweetener is only one illustration of the synthesis of sucrose derivatives wherein it is desired either to derivatize certain specific hydroxyl groups, and only such hydroxyl groups, or to derivatize only a specified number of the hydroxyls, perhaps in this latter case without particular regard to which particular hydroxyl(s) are derivatized. The preparation of sucrose-based monoester surfactants is a commercial example of mono substitution on the sucrose molecule.

This invention provides a means for synthesizing sucrose compounds such as 6-substituted sucrose derivatives wherein the process of the invention is highly regioselective both with regard to directing the reaction strictly to the 6 position and to the preparation of monosubstituted derivatives only. The term "regioselective" refers to a reaction that highly favors a single major product. (Ref., Hassner, "Regiospecificity. A Useful Terminology in Addition and Elimination Reactions", *J. Org. Chem.*, 33, No. 7, 2684–2686, July 1968.)

BRIEF SUMMARY OF THE INVENTION

Dialkyltin oxides are converted to cyclic tin adducts upon treatment with a variety of structurally diverse diols and diol-equivalents. Treatment of sucrose with, e.g., about one molar equivalent of these dialkyltin-diol cycloadducts produces a previously unknown group of reactive intermediates which have been identified as 6-O-[dialkyl(hydroxyalkyl)stannoxyl]sucrose derivatives. Treatment of said derivatives with, e.g., two equivalents of an acylating agent such as a carboxylic acid anhydride results in the highly regioselective generation of sucrose-6-acylates. More specifically, the invention provides a process which comprises the steps of:

(a) reacting a di(hydrocarbyl)tin oxide such as a dialkyltin oxide with a dihydric alcohol, alkanolamine, or an enolizable α-hydroxyketone (i.e., an α-hydroxyketone that is capable of enolization to an enediol) in an inert organic reaction vehicle, with removal of water, at a temperature and for a period of time sufficient to produce a cyclic adduct of said dialkyltin oxide and said dihydric alcohol, alkanolamine, or enolizable α-hydroxyketone;

(b) reacting said cyclic adduct product of Step (a) with sucrose in an inert organic reaction vehicle in which sucrose has an appropriate degree of solubility, such as a dipolar aprotic liquid, at a temperature and for a period of time sufficient to produce a 6-O-[dihydrocarbyl(hydroxy- or amino- or oxohydrocarbyl)stannoxyl]sucrose; and (c) reacting the product of Step (b) with an acylating agent to produce a sucrose-6-ester.

The Prior Art

In a review article entitled REGIOSELECTIVE MANIPULATION OF HYDROXYL GROUPS VIA ORGANOTIN DERIVATIVES, *Tetrahedron*, Vol. 41, No. 4, pp. 643–663 (1985), David et al. disclose the reaction of tin compounds with hydroxyl-group containing compounds to produce stannoxyl compounds, which can then be alkylated or acylated to produce ethers or esters. The reaction of bis(tributyltin) oxide with various carbohydrates (including sucrose), followed by acylation to produce a mixture of esters of varying degrees of substitution, is disclosed. The use of dibutyltin oxide in a reaction with carbohydrates is also disclosed in the article.

Holzapfel et al., in "Sucrose Derivatives and the Selective Benzoylation of the Secondary Hydroxyl groups of 6,1',6'-tri-O-tritylsucrose", S. Afr. Tydskr. Chem, 1984,37(3), pages 57–61, disclose the reaction of dibutyltin oxide with 6,1',6'-tri-O-tritylsucrose, followed by reaction with benzoyl chloride to produce a 72% yield of 3'-O-benzoyl-6,1',6'-tri-O-tritylsucrose and 9% of the 2-O-benzoate derivative, and minor amounts of the 2,3'-dibenzoate derivative.

Navia, PROCESS FOR SYNTHESIZING SUCROSE DERIVATIVES BY REGIOSELECTIVE REACTION, U.S. patent application Ser. No. 220,641, filed on July 18, 1988, now U.S. Pat. No. 4,950,746 and assigned to the same assignee as this application, describes the selective monoacylation of sucrose mediated by dialkoxydistannoxanes and diphenoxydistannoxanes. The reactive intermediate (toward 6-acylation) in the cited Navia application is a 1,3-di-(6-O-sucrose)-1,1,3,3-tetra(hydrocarbyl)distannoxane (abbreviated as DBSS for dibutylstannoxylsucrose, for the preferred compound wherein "hydrocarbyl" is butyl)[1], which is formed by reaction of sucrose with a dialkoxy- or diphenoxydistannoxane, which is in turn generated by the reaction of di(hydrocarbyl)tin oxides with straight or branched chain alcohols or phenols. Literature references related to this chemistry are cited below[2-11].

The fact that diorganotin oxides and dialkoxides react with vicinal glycols is known[12-15]. The products of these reactions are cyclic dialkoxides (dioxastannolanes) which are generally easily isolable solids and are reported to have enhanced moisture stability relative to noncyclic organotin alkoxides or phenoxides[16,17].

The reaction of materials capable of tautomerization to vicinal-diol equivalents (i.e., enediols) with diorganotin oxides to generate similar cyclic dioxastannole derivatives is also known for the case of the reaction of benzoin with dibutyltin oxide[18].

The invention of this application involves the discovery of a new reaction pathway involving dialkyl(hydroxyalkyl)stannoxylsucrose derivatives which is novel and unexpected. It could not have been predicted that tin-oxygen coordination in the said derivatives would involve the sucrose 6-position oxygen, which would thus give rise to significantly enhanced nucleophilicity at this position.

REFERENCES AND FOOTNOTES

1) The structure of the reactive intermediate DBSS of U.S. patent application Ser. No. 220,641 has been shown by $^{13}$C, $^{119}$Sn, and high-field $^1$H NMR analyses to be a 1,3-sucrose-disubstituted distannoxane.

2) R. C. Poller, "The Chemistry of Organotin Compounds", *Academic Press,* New York, 1970.

3) W. P. Neumann, "The Organic Chemistry of Tin", John Wiley, London, 1970.

4) R. M. Munavu and H. H. Szmant, J. Org. Chem., 41, 1832 (1976).

5) C. Auge, et al., J. Chem. Soc. Chem. Commun., 375 (1976).

6) G. P. Rizzi and H. M. Taylor, U.S. Pat. No. 3,963,699 (1976).

7) J. L. Hickson, "Sucrochemistry", American Chemical Society, Washington, D.C., 1977.

8) H. R. Galleymore, et al., U.S. Pat. No. 4,298,730 (1981).

9) J. Alais, et al., Tetrahedron Lett., 2383 (1983).

10) N. Morishima, et al., Bull. Chem. Soc. Jpn., 56, 2849 (1983).

11) S. David and S. Hanessian, Tetrahedron, 41, 643 (1985).

12) H. E. Ramsden and C. K. Banks, U.S. Pat. No. 2,789,994 (1957).

13) J. Bornstein, et al., J. Org. Chem., 24, 886 (1959).

14) R. C. Mehrotra and V. D. Gupta, J. Organomet. Chem., 4, 145 (1905).

15) J. Pommier and J. Valade, Bull. Soc. Chim. Fr., 1257 (1965).

16) W. J. Considine, J. Organomet. Chem., 5, 263 (1966).

17) A. G. Davies, et al., J. Chem. Soc. Dalton Trans., 297 (1986).

18) A. G. Davies and J. A.-A. Hawari, J. Organomet. Chem., 224, C37 (1982).

DETAILED DESCRIPTION OF THE INVENTION

The process of the invention is particularly useful as an improvement in the overall process for the manufacture of the nonnutritive sweetener sucralose. The regioselective preparation of a 6-blocked sucrose derivative is an important factor in a cost-effective sucralose manufacturing process, as was explained above in the Background Of The Invention section of this application.

The first step in the process of the invention comprises the reaction of a di(hydrocarbyl)tin oxide with a dihydric alcohol, an alkanolamine, or an enolizable α-hydroxyketone in an inert organic vehicle such as a normally liquid hydrocarbon, with removal of water, at a temperature and for a period of time sufficient to produce a cyclic adduct of said dihydric alcohol, alkanolamine, or a-hydroxy ketone. The inert organic vehicle employed is one that is capable of removing water, such as by azeotropic distillation. Hydrocarbons having boiling points between about 80° and 145° C. are preferred. Specific illustrative examples of such inert organic vehicles are cyclohexane, benzene, toluene, any of the xylenes, or mixtures thereof.

The di(hydrocarbyl)tin oxides employed in the invention are those in which the hydrocarbyl groups bonded to tin can be, individually, alkyl, cycloalkyl, aryl, or arylalkyl such as, for example, methyl, ethyl, propyl, butyl, octyl, benzyl, phenethyl, phenyl, naphthyl, cyclohexyl, and substituted phenyl. The preferred hydrocarbyl groups are alkyl having up to eight carbon atoms. The di(hydrocarbyl)tin oxide can be generated in situ from the corresponding dihalide, diester, dialkoxide, and the 1,3-dialkoxy- and 1,3-diacyloxydistannoxane by treatment with aqueous base. The water from the aqueous base would be removed by the azeotropic distillation, and the salt produced would be inert and could easily be removed at a later stage of the process. The dihalides and dialkoxides would be directly useful for reaction with diols to produce cycloadducts.

The di(hydrocarbyl)tin oxide is reacted with a dihydric alcohol, an alkanolamine, or an α-hydroxyketone. Specific illustrative examples of dihydric alcohols include alkane diols such as ethylene glycol, 2,3-propanediol, 2,3-butanediol, 1,3-butanediol, 1,4-butanediol, 1,3-propanediol, 1,2-pentanediol, 1,2-hexanediol, and other alkane diols that contain, for example, up to about eight carbon atoms, and cycloalkane diols such as 1,2-cyclohexanediol, 1,2-cyclopentanediol, and the like. Preferably, the hydroxyl groups on the dihydric alcohol are not more than four carbon atoms distant from each other on the carbon chain to which they are bonded. Specific illustrative examples of alkanolamines that can be used include ethanolamine, 2-amino-1-propanol, and 1-amino-2-propanol. Preferably, the hydroxyl group and the amino group on the alkanolamine are not more than four carbon atoms distant from each other on the carbon chain to which they are bonded. Specific illustrative examples of α-hydroxyketones that are capable of enolization to enediols include benzoin (2-hydroxy-2-phenylacetophenone) and acetoin (3-hydroxy-2-butanone). The preferred compounds for use in reacting with the di(hydrocarbyl)tin oxide are the alkane diols, particularly, ethylene qlycol, since it gives excellent yields and is itself inexpensive.

The di(hydrocarbyl)tin oxide, which is normally insoluble in the inert organic reaction vehicle employed, may be suspended in the vehicle. The diol, alkanolamine, or α-hydroxyketone (in slight stoichiometric excess) to be employed for the adduct formation is then added and the mixture is heated to reflux, which is normally at a temperature of from about 80° C. to about 145° C. Water is removed, preferably by azeotropic distillation, as it is formed as a result of the condensation between the di(hydrocarbyl)tin oxide and the diol, alkanolamine, or α-hydroxyketone to afford homogeneous usually colorless solutions of the cyclic adducts. Reaction times of from about two to about four hours are typical for this step.

These adduct intermediates may then be isolated by concentration and crystallization. It is usually more convenient to evaporate the solvent to produce a solid or a semisolid di(hydrocarbyl)tin adduct, which is then dispersed in N,N-dimethylformamide (DMF) or other solvent in which sucrose has an appropriate degree of solubility, which is used as the reaction medium for Step (b) of the process of the invention. Such solvents include DMF, dimethyl sulfoxide (DMSO), N-methylpyrrolidinone (NMP), N,N-dimethylacetamide (DMA), hexamethylphosphoramide (HMPA), and other polar, aprotic solvents in which sucrose is soluble.

In Step (b), sucrose is added to the reaction mixture which comprises the adduct product of Step (a) and the inert organic reaction vehicle such as DMF. The resulting suspension is stirred at ambient temperature for a period of time sufficient to form the 6-O-[dihydrocarbyl(hydroxy- or amino- or oxohydrocarbyl)stannoxyl]-sucrose intermediate, which usually takes from about twelve to about twenty-four hours at ambient temperatures (e.g., about 20°-25° C.). Alternatively, heating (e.g., up to about 85° C.) may be applied to increase the sucrose dissolution rate and shorten reaction time to, e.g., the order of about sixty minutes.

In Step (c) of the process of the invention, the turbid mixtures, which contain the reactive 6-O-[dihydrocarbyl(hydroxy- or amino- or oxohydrocarbyl)stannoxyl]-sucrose intermediate and which comprise the product of Step (b) of the process of the invention, are then treated with two molar equivalents of an acylating agent such as a carboxylic acid anhydride, preferably at ambient temperature. The mixtures are stirred and monitored by TLC until acylation is judged to be complete (typically from about two to about seven hours). These turbid mixtures usually become crystal clear during this phase of the process.

The mixtures are quenched by the addition of water or methanol, filtered if necessary to remove any extraneous solids, extracted if desired to remove di(hydrocarbyl)tin byproducts, concentrated to a residual gum or oil in a heated water bath under reduced pressure, and then further processed and assayed as necessary (function of acyl group) prior to further processing, such as chlorination when the sucrose-6-acylate is to be used in the production of sucralose.

The selection of the particular acylating agent to be used in the acylation reaction is dictated in part by the use to which the acylated product is to be put. For example, if the acyl group is being employed as a blocking group, as it would be in the preparation of the artificial sweetener sucralose as discussed above in the Background of the Invention section of this application, an acylating agent such as benzoic or acetic anhydride would be employed because it is inexpensive, the acyl group is readily removed at an appropriate stage of the synthesis, and it is stable to reactions that the acylated compound must undergo prior to removal of the acyl group. If a sucrose-6-ester is to be the ultimate product of the synthesis, then the acylating agent used is the one that will generate the desired acyl group for the ester product. With these principles in mind, among the acylating agents that can be used are the various anhydrides and acid halides of benzoic and substituted benzoic acid (e.g., 4-nitrobenzoic acid, 3,5-dinitrobenzoic acid, and the like), alkanoic acids such as acetic acid, propionic acid, butyric acid, cyclohexanecarboxylic acid, long chain fatty acids, both saturated and unsaturated, such as stearic acid, oleic acid, linoleic acid, and the like, having up to, for example, 28 carbon atoms, unsaturated acids such as acrylic acid and methacrylic acid, substituted acids such chloroacetic acid, cyanoacetic acid, phenoxyacetic acid, and the like, and saturated and unsaturated dicarboxylic acids such as phthalic acid, maleic acid, glutaric acid, and the like.

Investigation of the mechanism of the process of the invention was undertaken with the simplest example, which is prepared from ethylene glycol and dibutyltin oxide. This adduct compound, formally named 2,2-dibutyl-1,3-dioxa-2-stannolane, was isolated in 92.8% yield. Physical characteristics reported below are consistent with the structure shown (in which "Bu" represents butyl):

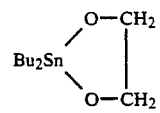

MW = 292.98
empirical formula = $C_{10}H_{22}O_2Sn$
mp(obs) = 224°-227° C.
mp(lit) = 223°-226.5° C. (ref 16)
Elemental Analysis: Galbraith #A2193

|  | % C | % H | % O | % Sn |
|---|---|---|---|---|
| calcd | 41.00 | 7.57 | 10.92 | 40.51 |
| found | 41.07 | 7.81 |  | 40.60 |

[119]Sn resonance (CDCl$_3$; (CH$_3$)$_4$Sn internal std) = δ - 180.1 ppm
[119]Sn resonance (CHCl$_3$; (Ph)$_4$Sn internal std) = δ - 189 ± 10 ppm (ref 17)

The cycloadduct was subsequently reacted (1:1 stoichiometry in DMF) with sucrose, the product concentrated to incipient dryness, filtered, and dried to yield a moisture-labile amorphous powder (quantitative nominal yield, containing residual DMF). Elemental analysis, corrected for residual DMF content (calculated from wt % N), is consistent with the following structure (in which "SUC" represents sucrose):

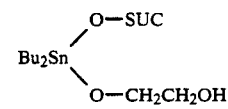

MW = 635.28
empirical formula = $C_{22}H_{44}O_{13}Sn$
Elemental Galbraith #A8252

|  | % C | % H | % O | % Sn |
|---|---|---|---|---|
| calcd | 41.59 | 6.98 | 32.74 | 18.68 |
| found | 41.59 | 6.93 |  | 18.76 |

Unlike the acylations described in U.S. patent application Ser. No. 220,641, now U.S. Pat. No. 4,950,756 which require a 1:1 stoichiometry of anhydride to dialkyltin adduct, the chemistry of the process of this invention requires approximately a 2:1 (molar) anhydride to adduct stoichiometric ratio. This is because the monoester of the diol component is formed at the same time the sucrose-6-ester is produced, as is illustrated in the reaction sequence depicted below.

In acylations conducted with benzoic anhydride, 2-hydroxyethyl benzoate is found as a minor contaminant in solid sucrose-6-benzoate ("S-6-B") samples prepared by the method of this invention. This ester is found primarily in the crystallization mother liquors. An authentic sample of this benzoate ester was prepared for comparison purposes by the following reaction (in which "Ph" represents phenyl):

HOCH₂CH₂OH + PhCOCl 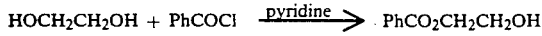 PhCO₂CH₂CH₂OH

MW = 166.18
68% recrystallized yield
empirical formula = $C_9H_{10}O_3$
270 MHz ¹H NMR spectrum consistent with structure.
Elemental Analysis: Galbraith #A3203

|  | % C | % H | % O |
|---|---|---|---|
| calcd | 65.05 | 6.07 | 28.88 |
| found | 65.19 | 6.08 |  |

The HPLC retention time of the authentic material was identical to that of the byproduct found in both the S-6-B samples and the mother liquors.

As a further check on the proposed mechanistic interpretation, the amorphous moisture-sensitive adduct between the 2,2-dibutyl-1,3-dioxa-2-stannolane and sucrose was reslurried in DMF and treated with benzoic anhydride. After crystallization, sucrose-6-benzoate was the resultant product accounting for 98.8%–99.4% of all benzoylated carbohydrate in the isolated product. The only other carbohydrate specie present to any significant extent was sucrose resulting from hydrolysis of the tin adduct in the presence of adventitious moisture.

Based on the results above, the mechanistic pathway for the reactions involved in the process of the invention is proposed to be the following, with dibutyltin oxide, ethylene glycol, and benzoic anhydride used for illustration:

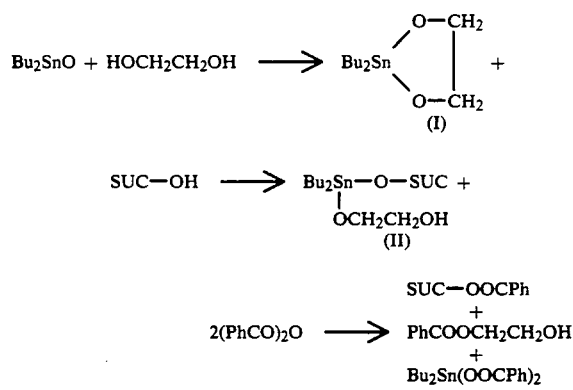

In the foregoing reaction sequence, if, e.g., ethanolamine were employed in place of ethylene glycol, the —O—CH₂CH₂OH group in the intermediate product (II) would be replaced by an —O—CH₂CH₂NH₂ group. In such a case, the intermediate product (II) would be a 6-O-[dihydrocarbyl(aminohydrocarbyl)stannoxyl]sucrose instead of a 6-O-[dihydrocarbyl(hydroxyhydrocarbyl)stannoxyl]sucrose.

In the foregoing reaction sequence, if, e.g., benzoin were employed in place of ethylene glycol, the —O—CH₂CH₂OH group in the intermediate product (II) would be replaced by an —O—CH(Ph)—COPh group. In such a a case, the intermediate product (II) would be a 6-O-[dihydrocarbyl(oxohydrocarbyl)stannoxyl]sucrose instead of a 6-O-[dihydrocarbyl(hydroxyhydrocarbyl)stannoxyl]sucrose.

The examples presented below further illustrate the process of the invention.

EXAMPLE 1

PREPARATION OF SUCROSE-6-BENZOATE USING DIBUTYLTIN OXIDE AND ETHYLENE GLYCOL

A 2000-ml, three-neck, round-bottom flask, equipped with mechanical stirrer, argon inlet, and Dean-Stark water separator topped with a reflux condenser, was charged with 27.4 g (110 mmol) of dibutyltin oxide, 6.83 g (6.15 ml, 110 mmol) of ethylene glycol, and 1250 ml of toluene. The slurry was heated to reflux, and held at this temperature for 12 hr. The resulting solution was allowed to cool to room temperature and stir for four hours. The fine, needle-like solid thus produced was filtered on a coarse-frit, sintered-glass filter, washed with toluene (100 ml), and vacuum dried (50° C./8 hr/0.5 mm of Hg) to afford 28.5 g (97.3 mmol, 88.4% yield) of 2,2-dibutyl-1,3-dioxa-2-stannolane.

A sample of the above stannolane (25.0 g, 85.3 mmol), sucrose (29.2 g, 85.3 mmol), and DMF (400 ml) were placed in a 1000-ml, round-bottom flask and magnetically stirred under argon at ambient temperature for 20 hr. The resulting suspension was treated in one portion with 38.6 g (171 mmol) of benzoic anhydride, and stirring continued at room temperature under argon. The reaction mixture became homogeneous after 60 min. The formation of S-6-B ($R_f$ 0.5) and the disappearance of sucrose ($R_f$ 0.2) were followed by SiO₂ TLC (15:10:2, CHCl₃—CH₃OH— H₂O, sprayed with 5% ethanolic H₂SO₄ and charred).

After stirring overnight, the conversion appeared complete by TLC. The reaction mixture was treated with methanol (25 ml), stirred two hr at room temperature, and vacuum evaporated (rotary evaporator, mechanical pump, 50° C. bath) to produce a viscous oil which was directly treated on the rotary evaporator at 50° C. with 250 ml of acetone. After cooling, the white solid thus produced was filtered, washed with 100 ml of ice-cold acetone, and vacuum dried (50° C./13 hr/0.5 mm of Hg) to afford 37.6 g of product shown by HPLC analysis to consist of 85.9 wt % sucrose-6-benzoate (32.3 g, 72.5 mmol, 85.0% yield basis sucrose).

EXAMPLE 2

PREPARATION OF SUCROSE-6-ACETATE USING DIBUTYLTIN OXIDE AND ETHYLENE GLYCOL

A 1000-ml, three-neck, round-bottom flask, equipped with mechanical stirrer, thermometer, and Dean-Stark water separator topped with a reflux condenser, was charged with 54.8 g (220 mmol) of dibutyltin oxide, 14.9 g (13.4 ml, 240 mmol) of ethylene glycol, and 500 ml of ortho-xylene. The suspension was heated to reflux, and the resulting clear solution refluxed for 2 hr, cooled to room temperature, and the solvent removed by rotary evaporation (mechanical pump, 25° C. bath). Vacuum drying (50° C./12 hr/1.0 mm of Hg) provided 64.6 g of crude 2,2-dibutyl-1,3-dioxa-2-stannolane as an off-white crystalline solid.

The crude tin-glycol cycloadduct was treated with sucrose (68.4 g, 200 mmol) in DMF (500 ml) with magnetic stirring under argon at 85° C. for 60 min. The resulting solution was cooled to 0° C. (partial precipitation) and treated dropwise with 42.9 g (420 mmol) of acetic anhydride dissolved in 50 ml of ice-cold DMF.

This mixture was stirred for 60 min at 0° C., followed by 60 min at room temperature. The reaction mixture became homogeneous immediately after anhydride addition. The formation of sucrose-6-acetate ($R_f$ 0.4) was followed using the TLC system described in Example 1.

The reaction mixture was transferred to a separatory funnel, treated with water (50 ml), and extracted with cyclohexane (2×1000 ml). The cyclohexane layers were discarded, and the DMF layer evaporated (rotary evaporator, mechanical pump, 50° C. bath) to afford a viscous, pale-yellow oil shown by HPLC analysis to contain 59.3 g (155 mmol, 77.3% yield basis sucrose) sucrose-6-acetate.

EXAMPLE 3

PREPARATION OF SUCROSE-6-ACETATE USING DIOCTYLTIN OXIDE AND ETHYLENE GLYCOL

A 1000-ml, three-neck, round-bottom flask, equipped with mechanical stirrer, thermometer, and Dean-Stark water separator topped with a reflux condenser, was charged with 39.7 g (110 mmol) of dioctyltin oxide, 7.44 g (6.70 ml, 120 mmol) of ethylene glycol, and 500 ml of toluene. The suspension was heated to reflux, and the resulting clear solution refluxed for 2 hr, cooled to room temperature, and the solvent removed by rotary evaporation (water aspirator, 50° C. bath). Vacuum drying (50° C./12 hr/1.0 mm of Hg) afforded 44.2 g of crude 2,2-dioctyl-1,3-dioxa-2-stannolane as a waxy white crystalline solid.

The crude cycloadduct was treated with sucrose (34.2 g, 100 mmol) in DMF (500 ml) with magnetic stirring under argon at 85° C. for 120 min. The resulting hazy solution was cooled to 0° C. (partial precipitation) and treated dropwise with 21.4 g (210 mmol) of acetic anhydride dissolved in 50 ml of ice-cold DMF. This mixture formed a very hazy solution while being stirred at room temperature for 120 min.

The reaction mixture was transferred to a separatory funnel, treated with water (50 ml), and extracted with cyclohexane (2×1000 ml). The cyclohexane layers were discarded, and the DMF layer evaporated (rotary evaporator, mechanical pump, 50° C. bath) to afford a viscous yellow oil shown by HPLC analysis to contain 29.0 g (75.4 mmol, 75.4% yield basis sucrose) sucrose-6-acetate.

EXAMPLE 4

PREPARATION OF SUCROSE-6-BENZOATE USING DIBUTYLTIN OXIDE AND 2,3-BUTANEDIOL

A 500-ml, four-neck, round-bottom flask, equipped with mechanical stirrer, thermometer, argon inlet, and Dean-Stark water separator topped with a reflux condenser, was charged with 12.5 g (50.0 mmol) of dibutyltin oxide, 4.55 g (4.59 ml, 50.5 mmol) of 2,3-butanediol (mixture of dl and meso isomers), and 350 ml of toluene. The suspension was heated to reflux and the resulting clear solution refluxed for 3 hr, cooled to room temperature, and the solvent removed by rotary evaporation (water aspirator, 50° C. bath). Vacuum drying (25° C./2 hr/0.5 mm of Hg) afforded 16.3 g of crude 2,2-dibutyl-4,5-dimethyl-1,3-dioxa-2-stannolane, mp 135°–8° C.

A sample of the above stannolane (15.2 g, 47.2 mmol), sucrose (16.1 g, 47.1 mmol), and DMF (250 ml) were placed in a 500-ml round-bottom flask and magnetically stirred under argon at ambient temperature for 16 hr. The cloudy mixture thus produced was treated in one portion with 21.3 g (94.2 mmol) of benzoic anhydride, and stirring continued at room temperature under argon with monitoring by $SiO_2$ TLC as described in Example 1.

After stirring for 8.5 hr, the reaction appeared complete. The mixture was treated with methanol (50 ml), stirred briefly at room temperature, and vacuum evaporated (rotary evaporator, mechanical pump, 50° C. bath) to produce an off-white gum which was directly treated on the rotary evaporator at 50° C. with 150 ml of acetone. After cooling, the white solid thus produced was filtered, washed with acetone (3×25 ml), and vacuum dried (25° C./14 hr/1.0 mm of Hg) to afford 17.2 g of product shown by HPLC analysis to consist of 90.7 wt % sucrose-6-benzoate (15.6 g, 35.0 mmol, 74.3% yield basis sucrose).

EXAMPLE 5

PREPARATION OF SUCROSE-6-BENZOATE USING DIBUTYLTIN OXIDE AND (±)-1,3-BUTANEDIOL

A 500-ml, four-neck, round-bottom flask, equipped with mechanical stirrer, thermometer, argon inlet, and Dean-Stark water separator topped with a reflux condenser, was charged with 12.7 g (51.0 mmol) of dibutyltin oxide, 4.55 grams (4.53 ml, 50.5 mmol) of (±)-1,3-butanediol, and 350 ml of toluene. The suspension was heated to reflux and the resulting clear solution refluxed for 2.5 hr, cooled to room temperature, and the solvent removed by rotary evaporation (water aspirator, 50° C. bath) to afford a colorless solid residue of tin-diol adduct (16.6 g).

The above-described product was treated with sucrose (17.1 g, 50.0 mmol) in DMF (250 ml) with magnetic stirring under argon at room temperature for 60 hr. The resulting hazy mixture was treated in one portion with 23.1 g (102 mmol) of benzoic anhydride, and stirring continued at room temperature under argon with monitoring by $SiO_2$ TLC as describe in Example 1. The mixture was homogeneous after 60 min.

After stirring for 6 hr, the conversion appeared complete. The mixture was treated with methanol (50 ml), stirred briefly at room temperature, and vacuum evaporated (rotary evaporator, mechanical pump, 50° C. bath) to produce a viscous pale-yellow oil which was directly treated on the rotary evaporator at 50° C. with 150 ml of acetone. After cooling, the solid product was filtered, washed with acetone (2×25 ml), and vacuum dried (25° C./19 hr/0.5 mm of Hg) to afford 16.9 g of material shown by HPLC analysis to consist of 98.0 wt % sucrose-6-benzoate (16.5 g, 37.0 mmol, 74.0% yield basis sucrose).

EXAMPLE 6

PREPARATION OF SUCROSE-6-BENZOATE USING DIBUTYLTIN OXIDE AND (±)-1,2-PROPANEDIOL

A 500-ml, four-neck, round-bottom flask, equipped with mechanical stirrer, thermometer, argon inlet, and Dean-Stark water separator topped with a reflux condenser, was charged with 12.7 g (51.0 mmol) of dibutyltin oxide, 3.84 g (3.71 ml, 50.5 mmol) of (±)-1,2-propanediol, and 350 ml of toluene. The suspension was heated to reflux and the resulting clear solution refluxed for 3 hr, cooled to room temperature, and the solvent removed by rotary evaporation (water aspirator, 50° C.

bath) to afford 16.0 g of crude 2,2-dibutyl-1,3-dioxa-4-methyl-2-stannolane as a colorless solid.

The crude cycloadduct was treated with sucrose (17.1 g, 50.0 mmol) in DMF (250 ml) with magnetic stirring under argon at first 55° C. for 2 hr and then room temperature for 15 hr. The resulting suspension was treated in one portion with 23.1 g (102 mmol) of benzoic anhydride, and stirring continued at room temperature under argon with monitoring by $SiO_2$ TLC as described in Example 1. The mixture was homogeneous after 2 hr.

After stirring for 6 hr, the reaction appeared complete. The mixture was treated with methanol (50 ml), stirred briefly at room temperature, and vacuum evaporated (rotary evaporator, mechanical pump, 50° C. bath) to produce a viscous pale-yellow oil which was directly treated on the rotary evaporator at 50° C. with 150 ml of acetone. After cooling, the solid product was filtered, washed with acetone (2×25 ml), and vacuum dried (40° C./24 hr/0.7 mm of Hg) to afford 19.6 g of material shown by HPLC analysis to consist of 93.0 wt % sucrose-6-benzoate (18.2 g, 40.9 mmol, 81.8% yield basis sucrose).

EXAMPLE 7

PREPARATION OF SUCROSE-6-BENZOATE USING DIBUTYLTIN OXIDE AND trans-1,2-CYCLOHEXANEDIOL A 500-ml, four-neck, round-bottom flask, equipped with mechanical stirrer, thermometer, argon inlet, and Dean-Stark water separator topped with a reflux condenser, was charged with 12.5 g (50.0 mmol) of dibutyltin oxide, 5.81 g (50.0 mmol) of trans-1,2-cyclohexanediol, and 350 ml of toluene. The suspension was heated to reflux and the resulting clear solution refluxed for 3 hr, cooled to room temperature, and the solvent removed by rotary evaporation (water aspirator, 50° C. bath) to give 17.8 g of crude tin-diol adduct as an off-white solid.

The above product was treated with sucrose (16.8 g, 49.1 mmol) in DMF (250 ml) with magnetic stirring under argon at first 55° C. for 3.5 hr and then room temperature for 30 min. The resulting suspension was treated in one portion with 22.6 g (100 mmol) of benzoic anhydride, and stirring continued at room temperature under argon with monitoring by $SiO_2$ TLC as described in Example 1.

After stirring for 17 hr, the turbid solution was quenched with methanol (50 ml), stirred briefly at room temperature, and vacuum evaporated (rotary evaporator, mechanical pump, 50° C. bath) to produce a light-yellow gummy solid which was directly treated on the rotary evaporator at 50° C. with 150 ml of acetone. After cooling, the product was filtered, washed with acetone (2×25 ml), and vacuum dried (40° C./2 hr/0.6 mm of Hg) to afford 17.3 g of white solid shown by HPLC analysis to consist of 94.0 wt % sucrose-6-benzoate (16.3 g, 36.4 mmol, 74.1% yield basis sucrose).

EXAMPLE 8

PREPARATION OF SUCROSE-6-BENZOATE USING DIBUTYLTIN OXIDE AND 1,4-BUTANEDIOL

A 500-ml, 4-neck, round-bottom flask, equipped with mechanical stirrer, thermometer, argon inlet, and Dean-Stark water separator topped with a reflux condenser, was charged with 12.5 g (50.0 mmol) of dibutyltin oxide, 4.55 g (4.47 ml, 50.5 mmol) of 1,4-butanediol, and 350 ml of toluene. The suspension was heated to reflux and the resulting clear solution refluxed for 2.5 hr, cooled to room temperature, and the solvent removed by rotary evaporation (water aspirator, 45° C. bath). Vacuum drying (25° C./2 hr/0.5 mm of Hg) gave 16.8 g of crude tin-diol adduct as a gelatinous white solid.

The above-described material was treated with sucrose (16.8 g, 49.1 mmol) in DMF (250 ml) with magnetic stirring under argon at room temperature for 15 hr. The resulting suspension was treated in one portion with 22.6 g (100 mmol) of benzoic anhydride, and stirring continued at room temperature under argon with monitoring by $SiO_2$ TLC as described in Example 1. The mixture was homogeneous after 20 min.

After stirring for 5 hr, the mixture was treated with methanol (50 ml), stirred briefly at room temperature, and vacuum evaporated (rotary evaporator, mechanical pump, 50° C. bath) to afford a cloudy yellow gum which was directly treated in the rotary evaporator at 50° C. with 150 ml of acetone. After cooling and scratching the insides of the flask with a spatula to induce crystallization, the product was filtered, washed with acetone (1×50 ml), and vacuum dried (25° C./13 hr/1.0 mm of Hg) to afford 16.3 g of white solid shown by HPLC analysis to consist of 86.1 wt % S-6-B (14.0 g, 31.4 mmol, 64.0% yield basis sucrose).

EXAMPLE 9

PREPARATION OF SUCROSE-6-BENZOATE USING DIBUTYLTIN OXIDE AND BENZOIN

A 500-ml, 4-neck, round-bottom flask, equipped with mechanical stirrer, thermometer, argon inlet, and Dean-Stark water separator topped with a reflux condenser, was charged with 12.5 g (50.0 mmol) of dibutyltin oxide, 10.8 g (51.0 mmol) of benzoin (2-hydroxy-2-phenylacetophenone), and 350 ml of benzene. The suspension was heated at reflux for 4 hr, cooled to room temperature to produce a yellowish gold mixture containing finely divided particulate matter, and the solvent removed by rotary evaporation (water aspirator, 50° C. bath). Vacuum drying (25° C./1 hr/0.5 mm of Hg) afforded 24.9 g of crude 2,2-dibutyl-1,3-dioxa-3,4-diphenyl-2-stannole.

The crude stannole was treated with sucrose (17.1 g, 50.0 mmol) in DMF (250 ml) with magnetic stirring under argon at room temperature for 14 hr. The resulting suspension was treated in one portion with 22.6 g (100 mmol) of benzoic anhydride, and stirring continued at room temperature under argon with monitoring by $SiO_2$ TLC as described in Example 1.

After stirring for 7 hr, the cloudy mixture was treated with methanol (50 ml), filtered through glass wool to remove a small amount of colloidal material, and vacuum evaporated (rotary evaporator, mechanical pump, 50° C. bath) to afford a clear yellowish gum which was directly treated on the rotary evaporator at 50° C. with 150 ml of acetone. After cooling, the solid product was filtered, washed with acetone (3×25 ml), and vacuum dried (25° C./14 hr/1.0 mm of Hg) to afford 16.6 g of white solid shown by HPLC analysis to consist of 90.4 wt % sucrose-6-benzoate (15.0 g, 33.6 mmol, 67.2% yield basis sucrose).

EXAMPLE 10

PREPARATION OF SUCROSE-6-BENZOATE USING DIBUTYLTIN OXIDE AND ETHANOLAMINE

A 500-ml, 4-neck, round-bottom flask, equipped with mechanical stirrer, thermometer, argon inlet, and Dean-Stark water separator topped with a reflux condenser, was charged with 12.7 g (51.0 mmol) of dibutyltin oxide, 3.05 g (3.01 ml, 50.0 mmol) of ethanolamine, and 350 ml of toluene. The suspension was heated at reflux for 2.5 hr, and the resulting clear solution was cooled to room temperature and the solvent removed by rotary evaporation (water aspirator, 50° C. bath) to afford 15.0 g of tin-ethanolamine adduct.

The crude adduct was treated with sucrose (17.1 g, 50.0 mmol) in DMF (250 ml) with magnetic stirring under argon at room temperature for 18 hr. The resulting suspension was treated in one portion with 23.1 g (102 mmol) of benzoic anhydride, and stirring continued at room temperature under argon with monitoring by $SiO_2$ TLC as described in Example 1. The mixture was homogeneous after 45 min.

After stirring for 7.5 hr, the mixture was treated with methanol (50 ml), stirred briefly at room temperature, and vacuum evaporated (rotary evaporator, mechanical pump, 50° C. bath) to afford a viscous yellow oil which was directly triturated on the rotary evaporator at 50° C. with 150 ml of acetone. After cooling to room temperature, the product was filtered, washed with acetone (2×25 ml), and vacuum dried (40° C./24 hr/0.7 mm of Hg) to afford 16.3 g of white solid determined by HPLC analysis to consist of 81.6 wt % sucrose-6-benzoate (13.3 g, 29.9 mmol, 59.7% yield basis sucrose). An additional 2.27 g of 81.1 wt % product was recovered by processing of the filtration mother liquors (67.9 total % yield).

The foregoing examples are summarized in the table below:

| REGIOSELECTIVE ACYLATION OF SUCROSE MEDIATED BY DIALKYLTIN-DIOL ADDUCTS | | | | | | | | |
|---|---|---|---|---|---|---|---|---|
| DIOL EMPLOYED | TIN ALKYL | SOLVENT[1] | TIME[2] | TEMP[3] | TIME[4] | ANHYDRIDE | TIME[5] | YIELD[6] |
| ethylene glycol | n-butyl | toluene | 12 | 25 | 20 | benzoic | 14 | 85.0 |
| ethylene glycol | n-butyl | o-xylene | 2 | 85 | 1 | acetic | 2 | 77.3 |
| ethylene glycol | n-octyl | toluene | 2 | 85 | 2 | acetic | 2 | 75.4 |
| 2,3-butanediol | n-butyl | toluene | 3 | 25 | 16 | benzoic | 8.5 | 74.3 |
| 1,3-butanediol | n-butyl | toluene | 2.5 | 25 | 60 | benzoic | 6 | 74.0 |
| 1,2-propanediol | n-butyl | toluene | 3 | 55/25 | 2/15 | benzoic | 6 | 81.8 |
| 1,2-cyclohexanediol | n-butyl | toluene | 3 | 55/25 | 3.5/0.5 | benzoic | 17 | 74.1 |
| 1,4-butanediol | n-butyl | toluene | 2.5 | 25 | 15 | benzoic | 5 | 64.0 |
| benzoin | n-butyl | benzene | 4 | 25 | 14 | benzoic | 7 | 67.2 |
| ethanolamine | n-butyl | toluene | 2.5 | 25 | 18 | benzoic | 7.5 | 67.9 |

[1]Solvent employed for cycloadduct formation.
[2]Time in hr used for cycloadduct formation.
[3]Temp in °C. employed for reaction of the cycloadduct with sucrose.
[4]Time in hr used for the reaction of the cycloadduct with sucrose.
[5]Time in hr employed for the acylation reaction.
[6]Percent yield corrected for sucrose-6-ester product purity.

What is claimed is:

1. Process which comprises the steps of:
   (a) reacting a di(hydrocarbyl)tin oxide with a compound selected from the group consisting of dihydric alcohols, alkanolamines, and enolizable a-hydroxyketones, in an inert organic reaction vehicle with removal of water and at a temperature and for a period of time sufficient to produce a cyclic adduct of said di(hydrocarbyl)tin oxide and said dihydric alcohol, alkanolamine, or enolizable a-hydroxyketone;
   (b) reacting said cyclic adduct product of Step (a) with sucrose in an inert organic reaction vehicle at a temperature and for a period of time sufficient to produce a 6-O-[dihydrocarbyl(hydroxyhydrocarbyl)stannoxyl]sucrose, a 6-O-[dihydrocarbyl(aminohydrocarbyl)stannoxyl]sucrose, or a 6-O-[dihydrocarbyl(oxohydrocarbyl)stannoxyl]sucrose; and
   (c) reacting the product of Step (b) with an acylating agent to produce a sucrose-6-ester.

2. The process of claim 1 wherein the di(hydrocarbyl)tin oxide is a dialkyltin oxide.

3. The process of claim 1 wherein the compound reacted with the di(hydrocarbyl)tin oxide is a dihydric alcohol.

4. The process of claim 2 wherein the compound reacted with the dialkyltin oxide is a dihydric alcohol.

5. The process of claim 3 wherein said dihydric alcohol is an alkanediol having from two to eight carbon atoms.

6. The process of claim 4 wherein said dihydric alcohol is an alkanediol having from two to eight carbon atoms.

7. The process of claim 6 wherein the alkanediol is ethylene glycol and wherein the dialkyltin oxide is dibutyltin oxide.

8. The process of claim 1 wherein the product of Step (a) is isolated from the reaction vehicle employed in Step (a) prior to Step (b).

9. The process of claim 1 wherein the acylating agent employed in Step (c) is a carboxylic acid anhydride.

10. The process of claim 9 wherein the carboxylic acid anhydride is employed in proportions of about two moles per mole of product of Step (b).

11. The process of claim 9 wherein the carboxylic acid anhydride is benzoic anhydride.

12. The process of claim 9 wherein the carboxylic acid anhydride is acetic anhydride.

13. The process of claim 1 wherein the inert organic reaction vehicle employed in Step (a) is a hydrocarbon.

14. The process of claim 13 wherein the hydrocarbon is selected from the group consisting of benzene, toluene, cyclohexane, and xylene.

15. The process of claim 1 wherein the inert organic reaction vehicle employed in Step (b) is a dipolar aprotic organic liquid.

16. The process of claim 15 wherein the dipolar aprotic organic liquid is N,N-dimethylformamide.

* * * * *